(12) United States Patent
Masuda et al.

(10) Patent No.: US 10,859,591 B2
(45) Date of Patent: Dec. 8, 2020

(54) METHOD AND APPARATUS FOR ANALYZING BLOOD

(71) Applicant: NIHON KOHDEN CORPORATION, Tokyo (JP)

(72) Inventors: Koji Masuda, Tokyo (JP); Hyuga Masu, Tokyo (JP); Satoshi Suzuki, Tokyo (JP); Rikiya Tanabe, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 89 days.

(21) Appl. No.: 15/740,110

(22) PCT Filed: Jun. 21, 2016

(86) PCT No.: PCT/JP2016/002999
§ 371 (c)(1),
(2) Date: Dec. 27, 2017

(87) PCT Pub. No.: WO2017/002329
PCT Pub. Date: Jan. 5, 2017

(65) Prior Publication Data
US 2018/0188277 A1  Jul. 5, 2018

(30) Foreign Application Priority Data

Jun. 30, 2015  (JP) .................................. 2015-131849

(51) Int. Cl.
*G01N 35/10* (2006.01)
*G01N 33/49* (2006.01)
(Continued)

(52) U.S. Cl.
CPC ......... *G01N 35/1009* (2013.01); *G01N 15/12* (2013.01); *G01N 33/49* (2013.01);
(Continued)

(58) Field of Classification Search
CPC ......... G01N 35/1009; G01N 35/00613; G01N 15/12; G01N 35/1016; G01N 33/49;
(Continued)

(56) References Cited

U.S. PATENT DOCUMENTS 3,549,994 A  *  12/1970  Rothermel .......... B01F 13/0233
324/71.1
5,266,269 A  *  11/1993  Niiyama ................ G01N 33/49
422/63

(Continued)

FOREIGN PATENT DOCUMENTS

CN  104165834 A  11/2014
EP  0 953 843 A2  11/1999
(Continued)

OTHER PUBLICATIONS

Japanese Office action issued in Japanese Office Action No. 2015-131849 dated Mar. 5, 2019.
(Continued)

*Primary Examiner* — Jill A Warden
*Assistant Examiner* — Quocan B Vo
(74) *Attorney, Agent, or Firm* — Pearne & Gordon LLP

(57) ABSTRACT

A blood analyzing method for detecting a short sample of blood in a suction tube, when blood is sucked by the suction tube constituting a blood analyzing apparatus, includes measuring a first blood parameter by using blood that is present in a first area of a blood analysis area, blood in the blood analysis area being used to analyze the blood in the suction tube, measuring a second blood parameter by using blood that is present in a second area of the blood analysis area, the second area being different from the first area, and detecting the short sample of blood based on the first blood parameter and the second blood parameter.

6 Claims, 11 Drawing Sheets

(51) Int. Cl.
*G01N 15/12* (2006.01)
*G01N 35/00* (2006.01)
*G01N 15/14* (2006.01)

(52) U.S. Cl.
CPC . *G01N 35/00613* (2013.01); *G01N 35/00623* (2013.01); *G01N 35/1016* (2013.01); *G01N 15/1459* (2013.01); *G01N 2035/1018* (2013.01); *G01N 2035/1032* (2013.01)

(58) Field of Classification Search
CPC ......... G01N 35/00623; G01N 15/1459; G01N 2035/1032; G01N 2035/1018
See application file for complete search history.

(56) References Cited

U.S. PATENT DOCUMENTS

| | | | | |
|---|---|---|---|---|
| 5,357,117 | A * | 10/1994 | Hayashi | G01N 35/1016 222/66 |
| 5,880,835 | A * | 3/1999 | Yamazaki | G01N 15/147 356/336 |
| 6,106,778 | A * | 8/2000 | Oku | G01N 15/10 422/105 |
| 6,107,810 | A * | 8/2000 | Ishizawa | G01F 23/266 324/662 |
| 6,235,534 | B1 | 5/2001 | Brookes et al. | |
| 2003/0075556 | A1 | 4/2003 | Tajima et al. | |
| 2004/0034479 | A1 * | 2/2004 | Shimase | G01N 35/1016 702/19 |
| 2006/0210438 | A1 * | 9/2006 | Nagai | G01N 15/14 422/73 |
| 2006/0250604 | A1 * | 11/2006 | Hamada | G01N 15/1459 356/39 |
| 2007/0009392 | A1 | 1/2007 | Tajima et al. | |
| 2007/0048868 | A1 | 3/2007 | Shibata et al. | |
| 2007/0109530 | A1 * | 5/2007 | Ueno | G01N 15/1404 356/39 |
| 2007/0166194 | A1 * | 7/2007 | Wakatake | G01N 35/0095 422/64 |
| 2009/0041628 | A1 * | 2/2009 | Kakizaki | G01N 35/1004 422/68.1 |
| 2011/0189713 | A1 * | 8/2011 | Le Comte | G01N 1/38 435/29 |
| 2011/0236990 | A1 * | 9/2011 | Mizutani | G01N 35/00603 436/180 |
| 2012/0203089 | A1 * | 8/2012 | Rule | A61B 5/0002 600/366 |
| 2012/0257201 | A1 | 10/2012 | Hattori | |
| 2012/0288407 | A1 | 11/2012 | Shibata et al. | |
| 2014/0190253 | A1 * | 7/2014 | Nishida | G01N 35/1011 73/304 C |
| 2014/0341780 | A1 * | 11/2014 | Ishii | G01N 33/49 422/73 |
| 2015/0112629 | A1 * | 4/2015 | Hattori | G01N 21/59 702/100 |
| 2016/0018426 | A1 * | 1/2016 | Moriya | G01N 35/026 422/65 |
| 2016/0282377 | A1 * | 9/2016 | Nagai | G01N 35/00663 |

FOREIGN PATENT DOCUMENTS

| | | |
|---|---|---|
| EP | 1 760 472 A1 | 3/2007 |
| JP | H11-337559 A | 12/1999 |
| JP | 2001-183382 A | 7/2001 |
| JP | 2007-064680 A | 3/2007 |
| JP | 4593404 B2 | 12/2010 |
| JP | 2012-220340 A | 11/2012 |

OTHER PUBLICATIONS

International Search Report issued in Patent Application No. PCT/JP2016/002999 dated Sep. 29, 2016.
Written Opinion issued in Patent Application No. PCT/JP2016/002999 dated Sep. 29, 2016.
Chinese Office action issued in Chinese Patent Application No. 201680039379.4 dated Feb. 21, 2020.

* cited by examiner

METHOD AND APPARATUS FOR ANALYZING BLOOD

TECHNICAL FIELD

The present invention relates to a method and an apparatus for analyzing blood.

BACKGROUND ART

In order to obtain blood information such as the counting of erythrocytes, blood platelets, and leukocytes, or the classification of leukocytes, a blood analyzing apparatus is used. The blood analyzing apparatus includes a suction tube that is used to suck blood filled in a blood collecting tube, and a plurality of analysis units to obtain information on the blood sucked by the suction tube.

In such a blood analyzing apparatus, a short sample infrequently occurs when blood is sucked by the suction tube.

Since the blood has high viscosity, there is a possibility that the short sample occurs in a tip side of the suction tube. In this case, air may be sucked instead of sucking a required amount of blood.

For example, when the suction tube is blocked by foreign matters, a sufficient amount of blood may not be sucked but the short sample may occur in a base end side of the suction tube. Then, the blood does not fill to the base end side of the suction tube.

As such, with the short sample of blood, for example, a sample in which a required amount of blood is not sucked, that is, the short sample of blood may undesirably occur in an area of the tip side and the base end side of the suction tube.

When the blood is analyzed using such a sample, it is not possible to acquire accurate blood information because a required amount of blood is not present. Thus, it is necessary to detect the short sample of blood.

In this connection, a technique of detecting the short sample of blood is disclosed in Japanese Patent Publication No. 4593404. In the invention disclosed in Japanese Patent Publication No. 4593404, blood is sucked by the suction tube, and then blood existing in the area of the tip side and the base end side rather than in the area used for analyzing the blood, in an internal space of the suction tube, is delivered to a detecting unit. The detecting unit measures turbidity of the delivered blood, and detects the short sample of blood based on a value of the turbidity.

SUMMARY

Technical Problem

In the above-described detecting method, however, blood provided for analysis and blood provided for detecting a short sample of blood are delivered, respectively, from different areas in an internal space of a suction tube. Therefore, when the short sample of blood occurs in the blood analysis area, it is not possible to detect the short sample of blood. Further, if the blood is analyzed when the short sample of blood occurs in the blood analysis area, this may lead to erroneous measurement results.

Solution to Problem

According to an aspect of the invention, a blood analyzing method for detecting a short sample of blood in a suction tube, when blood is sucked by the suction tube constituting a blood analyzing apparatus, includes measuring a first blood parameter by using blood that is present in a first area of a blood analysis area, blood in the blood analysis area being used to analyze the blood in the suction tube, measuring a second blood parameter by using blood that is present in a second area of the blood analysis area, the second area being different from the first area, and detecting the short sample of blood based on the first blood parameter and the second blood parameter.

According to another aspect of the invention, a blood analyzing apparatus includes a suction tube that is used to suck blood, a first chamber to which the blood is discharged from the suction tube, a first measuring unit that measures a first blood parameter using the blood discharged to the first chamber, a second chamber to which the blood is discharged from the suction tube, a second measuring unit that measures a second blood parameter using the blood discharged to the second chamber, and a detecting unit that, based on the first blood parameter and the second blood parameter, detects a short sample of blood in the suction tube when blood is sucked by the suction tube.

Advantageous Effects of Invention

According to the above-described blood analyzing method, both the operation of analyzing the blood and the operation of detecting the short sample of blood in the suction tube are performed using the blood present in the blood analysis area, namely, the first and second areas. Thus, even if the short sample of blood occurs in the blood analysis area in the suction tube, it is possible to detect the short sample of blood. Therefore, when the short sample of blood occurs in the blood analysis area, it is possible to detect the sample and to prevent erroneous measurement results from being offered.

Further, according to the above-described blood analyzing method, both the operation of analyzing the blood and the operation of detecting the short sample of blood in the suction tube are performed using the blood discharged to first and second chambers. Thus, even if the short sample of blood occurs in the blood analysis area in the suction tube, it is possible to detect the short sample of blood. Therefore, when the short sample of blood occurs in the blood analysis area, it is possible to detect the sample and to prevent erroneous measurement results from being offered.

DESCRIPTION OF EMBODIMENTS

Figure 1:
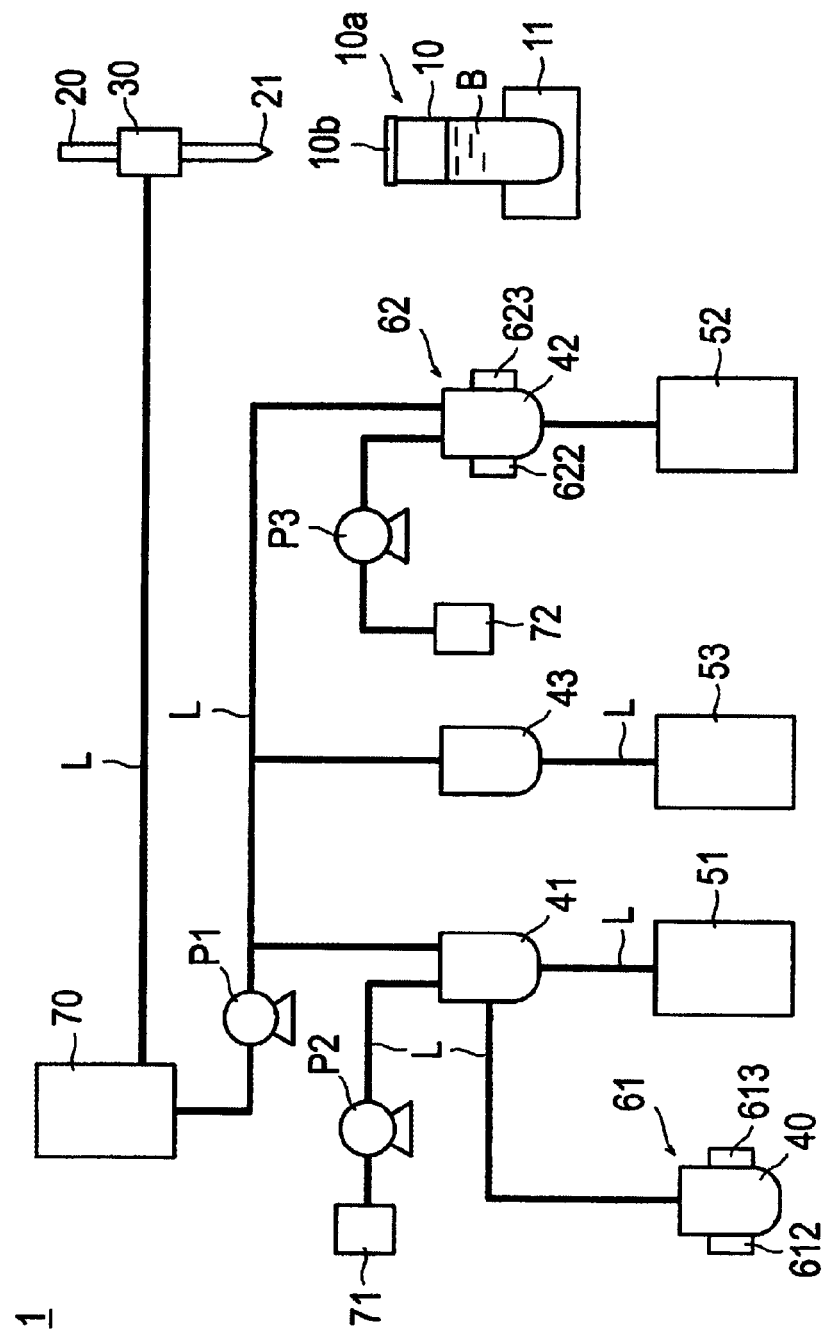
FIG. 1 is a schematic view illustrating a blood analyzing apparatus according to an embodiment of the invention.

An embodiment of the invention will be described with reference to the accompanying drawings. The same reference numerals throughout the drawings denote elements having the same or similar function, and a duplicated description thereof will be omitted herein. Dimensions in the drawings are not shown to scale but are exaggerated for the convenience of description.

FIG. 1 is a schematic view illustrating a blood analyzing apparatus 1 according to the embodiment of the invention.

The blood analyzing apparatus 1 includes a blood collecting tube 10 that is filled with collected blood B, a suction tube 20 that is used to suck the blood from the blood collecting tube 10, and a washing unit 30 that washes the suction tube 20. Further, the blood analyzing apparatus 1 includes three chambers 41, 42 and 43 to which the blood is discharged out from the suction tube 20, three analysis units 51, 52, and 53 analyzing the blood using the blood discharged to the chamber 41, 42, and 43, and two measuring units 61 and 62 that may measure blood parameters, that is, amount of hemoglobin (HGB), turbidity, or absorbance. The blood analyzing apparatus 1 includes a storage unit 70 that stores a dilute solution, and storage units 71 and 72 that store hemolytic agent. The blood analyzing apparatus 1 includes three pumps P1, P2, and P3 for delivering the dilute solution and the hemolytic agent, a pipe L in which the dilute solution and the hemolytic agent circulate, and an electromagnetic valve (not illustrated) for opening or closing the pipe L. The blood analyzing apparatus 1 has a control unit 80 to control the movement of respective components.

The blood collecting tube 10 is mounted on a mounting unit 11. An opening 10a is formed in an upper portion of the blood collecting tube 10. The opening 10a is closed by a rubber stopper 10b, and thus an interior of the blood collecting tube 10 is sealed. A material of the blood collecting tube 10 may employ a material used in the related art without being particularly limited. For example, the blood collecting tube 10 may be made of glass, plastics, or the like.

Figure 2:
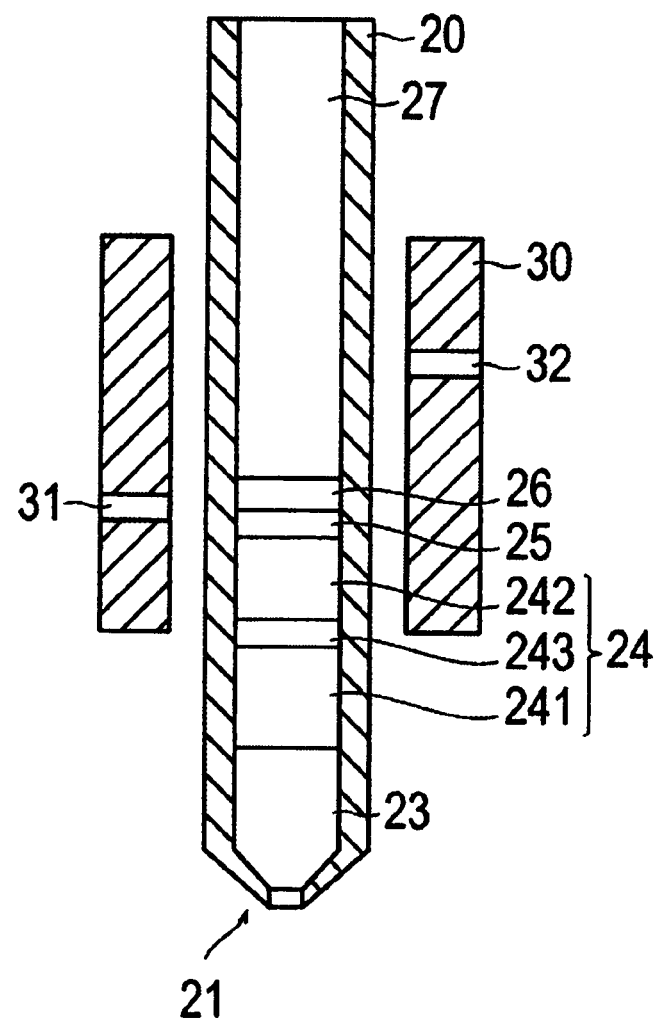
FIG. 2 is a schematic sectional view illustrating a suction tube and a washing unit.

FIG. 2 is a schematic sectional view illustrating the suction tube 20 and the washing unit 30.

The suction tube 20 has a needle-shaped puncture portion 21 on a tip side thereof. The puncture portion 21 punctures the rubber stopper 10b of the blood collecting tube 10, and the suction tube 20 is inserted into the blood collecting tube 10, so that the suction tube 20 sucks blood from the blood collecting tube 10.

A flow path is formed in the suction tube 20 to store the sucked blood. The flow path has a first waste area 23 to store waste blood, a blood analysis area 24 provided to analyze blood, and a second waste area 25 to store waste blood, in this order from a lower portion of FIG. 2. The flow path further has an air layer area 26 in which an air layer is formed, and a diluent area 27 in which diluents are placed. In the drawing, the respective areas in the flow path are clearly separated from each other. However, there is no particular structure for physically separating these areas from each other. That is, the first waste area 23, the blood analysis area 24, and the second waste area 25 simply represent the order of blood that is arranged in the flow path when blood is first sucked, and then is used (wasted) by a predetermined amount in a post process. Therefore, the first waste area 23, the blood analysis area 24, the second waste area 25, the air layer area 26, and the diluent area 27 are properly shifted in a circulation direction (vertical direction in FIG. 2) of the flow path, in respective steps of the blood analyzing method that will be described later.

The blood analysis area 24 is further divided as follows. The blood analysis area 24 includes a first area 241 in which blood used for the measurement of first leukocytes, for example, 3-classification of leukocytes is stored, a second area 242 in which blood used for the measurement of second leukocytes, for example, 5-classification of leukocytes is stored, and a third area 243 in which blood used for the counting of erythrocytes is stored. The third area 243 is formed between the first area 241 and the second area 242. Here, the blood of the first area 241 and the blood of the second area 242 may be used to measure the 5-classification of leukocytes or the 3-classification of leukocytes, respectively, or may be used to count the leukocytes.

In this regard, the 3-classification of leukocytes means an operation of classifying the leukocytes into granulocytes, lymphocytes, and monocytes and then counting them. Further, the 5-classification of leukocytes means an operation of classifying the leukocytes into neutrophils, eosinophils, basophils, lymphocytes, and monocytes and then counting them.

The suction tube 20 is made of a metal material, such as a stainless alloy, without being limited to a particular material.

As illustrated in FIG. 2, the washing unit 30 is slidably arranged relative to an outer circumference of the suction tube 20. The washing unit 30 has two passing portions 31 and 32 through which dilute solution may pass. The passing portions 31 and 32 are arranged in pairs on left and right sides to be located at different heights.

Turning back to FIG. 1, the blood analyzing apparatus 1 includes a fourth chamber 41, a second chamber 42, and a third chamber 43. The third chamber 43 is arranged between the fourth chamber 41 and the second chamber 42.

Blood stored in the first area 241 of the suction tube 20 is discharged to the fourth chamber 41. Blood stored in the second area 242 of the suction tube 20 is discharged to the second chamber 42. Blood stored in the third area 243 of the suction tube 20 is discharged to the third chamber 43.

The blood analyzing apparatus 1 also includes a first analysis unit 51, a second analysis unit 52, and a third analysis unit 53.

The first analysis unit 51 is connected via a pipe L to the fourth chamber 41. The first analysis unit 51 performs the 3-classification of leukocytes using the blood discharged to the fourth chamber 41. An electric resistance method is applied to the first analysis unit 51.

Figure 3:
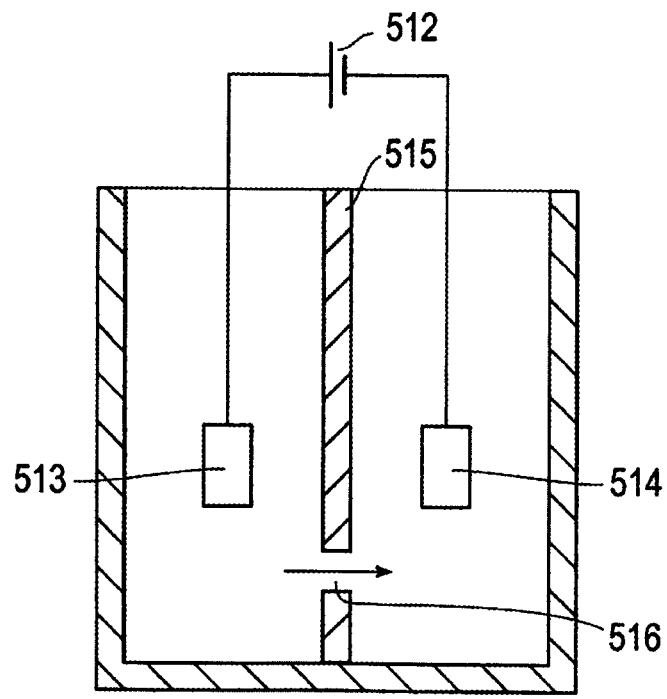
FIG. 3 is a schematic view illustrating a first analysis unit.

FIG. 3 is a schematic view illustrating the first analysis unit 51.

As illustrated in FIG. 3, the first analysis unit 51 includes a resistance detecting unit 512, a pair of electrodes 513 and 514, and a chamber 515. In the first analysis unit 51, when a blood cell passes through an aperture 516 defined between the two electrodes 513 and 514, electric resistance between the two electrodes 513 and 514 is changed depending on the size of the blood cell. The first analysis unit counts the leukocytes, based on a pulse number and a pulse width of the change in resistance.

Returning back to FIG. 1, the second analysis unit 52 is connected via a pipe L to the second chamber 42. The second analysis unit 52 performs the 5-classification of leukocytes using the blood discharged to the second chamber 42. A flow cytometry technique is applied to the second analysis unit 52.

Figure 4:
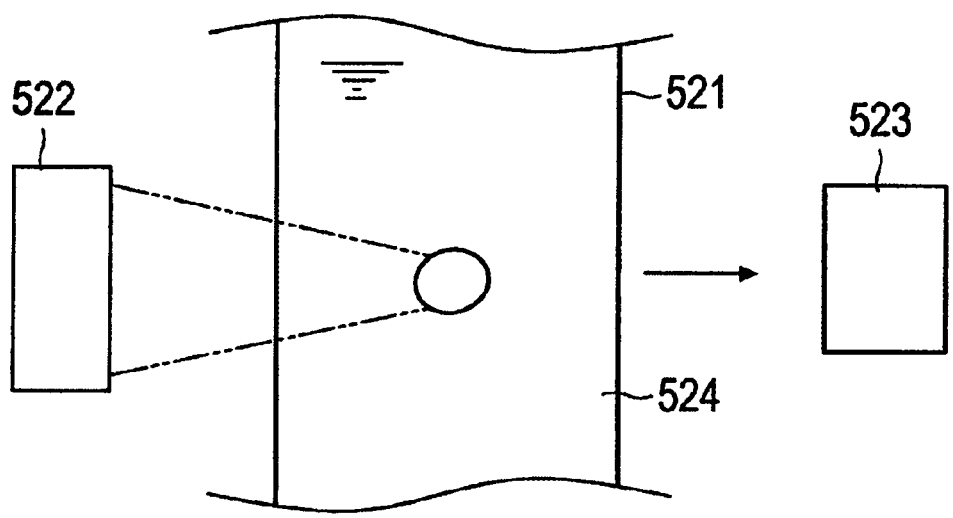
FIG. 4 is a schematic view illustrating a second analysis unit.

FIG. 4 is a schematic view illustrating the second analysis unit 52.

As illustrated in FIG. 4, the second analysis unit 52 includes a flow path 521, a light source 522, and a light receiving element 523. The second analysis unit 52 may further include an optical unit, such as a lens, for changing an optical path.

The flow path 521 is made in the shape of a tube, and has a flow 524 formed therein. The flow is formed by surrounding a sample, produced by mixing a dilute solution and a hemolytic agent for the 5-classification of leukocytes with the blood, by sheath liquid. The flow path 521 is made of any material, for example, quartz, glass, or synthetic rein, without being limited to a particular material, as long as the material has transmittance.

The light source 522 irradiates the blood cells circulating in the flow path 521 with a laser. A semiconductor laser or the like may be used as the light source.

The light receiving element 523 detects a light signal of scattered light produced when the light source 522 irradiates the blood cells with light. The 5-classification of leukocytes is performed based on this light signal. Further, in addition to or instead of the scattered light when the sample is irradiated with light, fluorescence is detected and thus the 5-classification of leukocytes may be performed.

Returning back to FIG. 1, the third analysis unit 53 is connected via a pipe L to a third chamber 43. The third analysis unit 53 counts the erythrocytes and the blood platelets, using the blood discharged to the third chamber 43. Similarly to the above-described first analysis unit 51, the electric resistance method is applied to the third analysis unit 53. Since the configuration of the third analysis unit 53 is the same as or similar to that of the first analysis unit 51, a detailed description thereof will be omitted.

The blood analyzing apparatus 1 includes a first measuring unit 61, and a second measuring unit 62.

As illustrated in FIG. 1, the first measuring unit 61 includes a first chamber 40, a light emitting element 612, and a light receiving element 613. The light emitting element 612 and the light receiving element 613 are arranged on opposite sides of the first chamber 40. The first chamber 40 may be made of a material having transmittance. For example, quartz, glass, synthetic rein or the like may be employed.

The light emitting element 612 is, for example, an LED, while the light receiving element 613 is, for example, a photo diode, without being particularly limited.

The light emitting element 612 irradiates the sample in the first chamber 40 with light. The light receiving element 613 receives transmitted light that has passed through the sample, and then measures the intensity of the transmitted light. The amount of hemoglobin (HGB), the turbidity, or the absorbance of the sample in the first chamber 40 are measured based on the intensity of the light of the light emitting element 612 and the intensity of the transmitted light.

As illustrated in FIG. 1, the second measuring unit 62 includes a second chamber 42, a light emitting element 622, and a light receiving element 623. The light emitting element 622 and the light receiving element 623 are arranged on opposite sides of the second chamber 42.

The light emitting element 622 irradiates the sample in the second chamber 42 with light. The light receiving element 623 receives transmitted light that has passed through the sample, and then measures the intensity of the transmitted light. The amount of hemoglobin (HGB), the turbidity, or the absorbance of the sample in the second chamber 42 are measured based on the intensity of the light of the light emitting element 622 and the intensity of the transmitted light.

The storage unit 70 is a reservoir that stores the dilute solution therein. The dilute solution stored in the storage unit 70 is used to wash the suction tube 20 and to dilute the blood discharged into the three chambers 41, 42, and 43. The dilute solution is fed to each component by the pump P1.

The storage unit 71 is a reservoir that stores the hemolytic agent for the 3-classification of leukocytes. The hemolytic agent stored in the storage unit 71 is delivered into the fourth chamber 41, and dissolves the erythrocytes of the blood in the fourth chamber 41 to stabilize them. Thus, it is possible to measure the 3-classification of leukocytes, the amount of hemoglobin (HGB), the turbidity, or the absorbance for the sample. The hemolytic agent in the storage unit 71 is delivered by the pump P2 into the fourth chamber 41.

The storage unit 72 is a reservoir that stores the hemolytic agent for the 5-classification of leukocytes. The hemolytic agent stored in the storage unit 72 is delivered into the second chamber 42, and dissolves the erythrocytes of the blood in the second chamber 42 to stabilize them. Thus, it is possible to measure the 5-classification of leukocytes, the amount of hemoglobin (HGB), the turbidity, or the absorbance for the sample. The hemolytic agent in the storage unit 72 is delivered by the pump P3 into the second chamber 42.

The control unit 80 is, for example, a CPU, and executes a control operation or various calculation processes of each component by a program. The control unit 80 serves as a detecting unit, for example, and detects the short sample of blood in the suction tube 20. A detailed detecting method of the short sample of blood will be described below. Further, the dilute solution or the hemolytic agent is delivered when the control unit 80 operates the pumps P1, P2, and P3. Moreover, when the dilute solution or the hemolytic agent is circulated in a predetermined pipe L, the electromagnetic valve located at the predetermined pipe L is controlled to be opened by the control unit 80.

Figure 5:
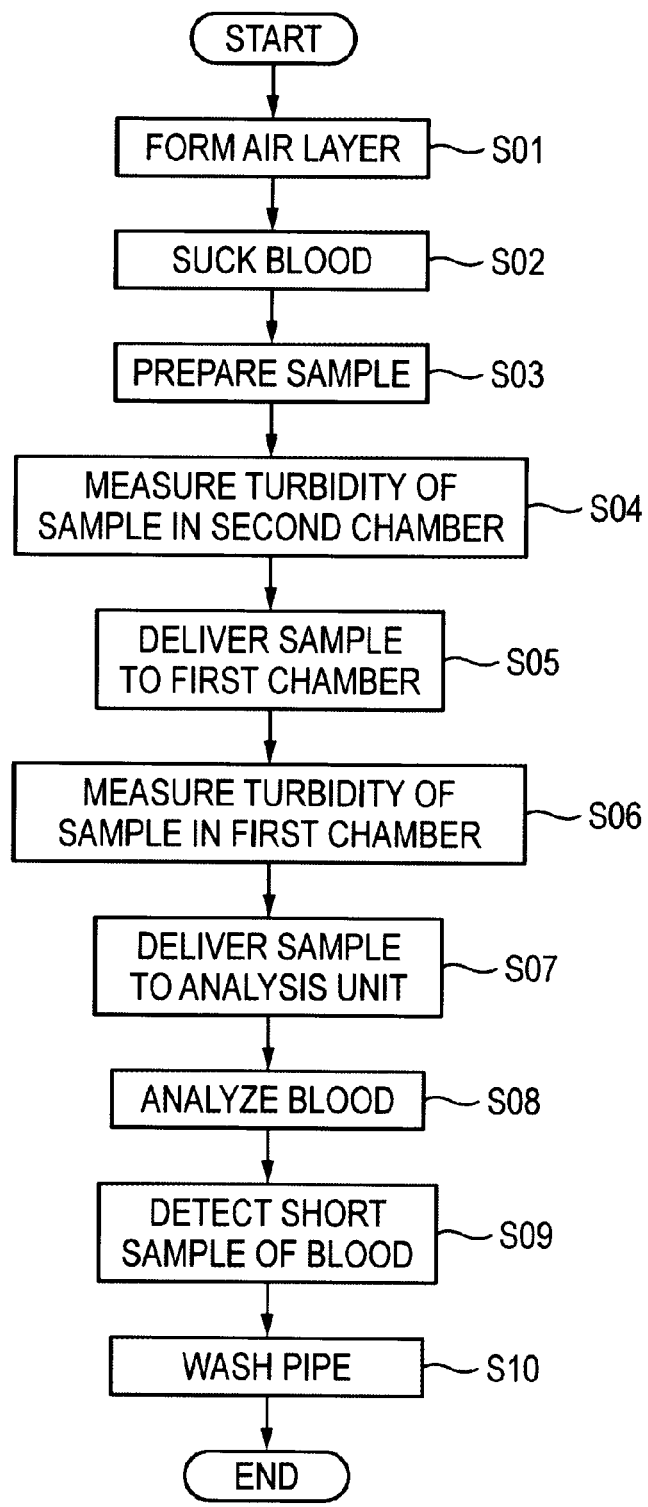
FIG. 5 is a flowchart illustrating a blood analyzing method according to the embodiment.

Next, the blood analyzing method according to the embodiment will be described with reference to FIGS. 5 to 7E. FIG. 5 is a flowchart illustrating the blood analyzing method according to the embodiment. A process illustrated in FIG. 5 may be achieved by operating respective different components of the blood analyzing apparatus 1 using the control unit 80. Hereinafter, a procedure of FIG. 5 will be described with reference to FIGS. 6A and 6B and FIGS. 7A to 7E.

Figure 6A:
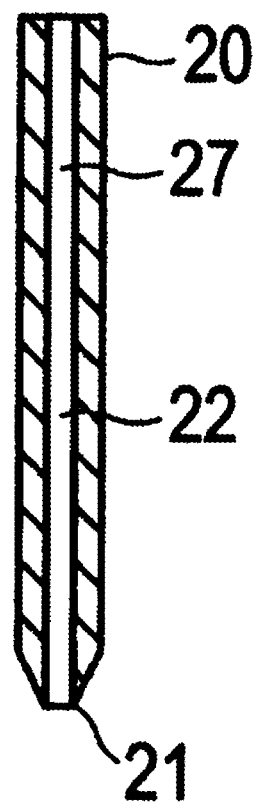
FIG. 6A illustrates a process of forming an air layer.
Figure 6B:
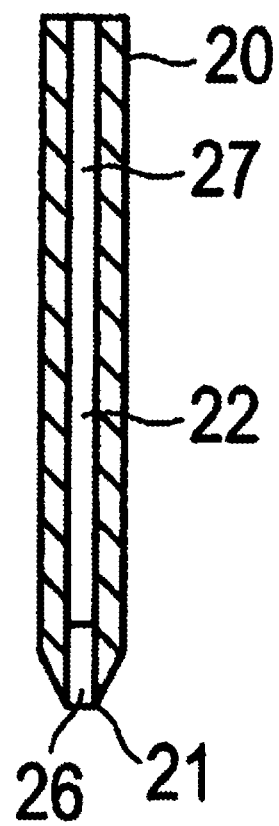
FIG. 6B illustrates a process of forming an air layer.

First, the air layer (corresponding to the air layer area 26 in FIG. 2) is formed on the tip side of the suction tube 20 (S01). As illustrated in FIGS. 6A and 6B, by raising the diluent area 27 in the suction tube 20 filled with only the diluents at first, the air layer area 26 is formed. At this time, the air layer area 26 of 5 microliter, for example, is formed.

Next, the blood in the blood collecting tube 10 is sucked by the suction tube 20 (S02). The process of step S02 will be described in detail with reference to FIGS. 7A to 7E.

Figure 7A:
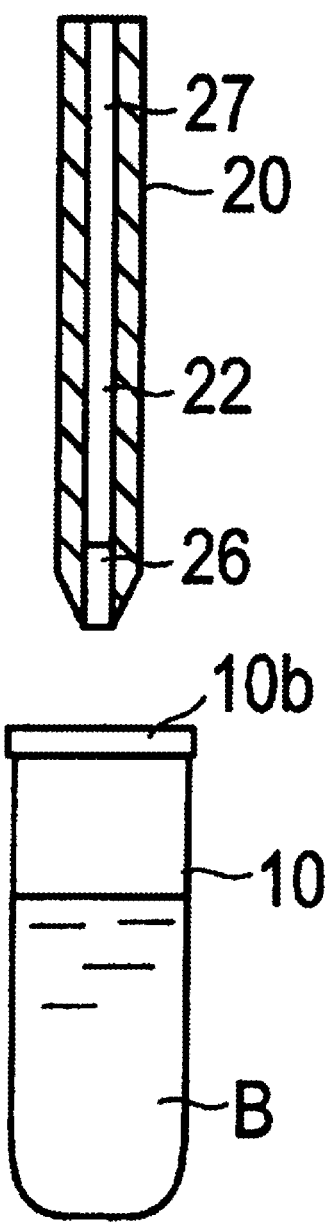
FIG. 7A illustrates a process of sucking blood.

First, as illustrated in FIG. 7A, the suction tube 20 in which the air layer area 26 is formed at step S01 is set on the blood collecting tube 10 filled with the blood B.

Figure 7B:
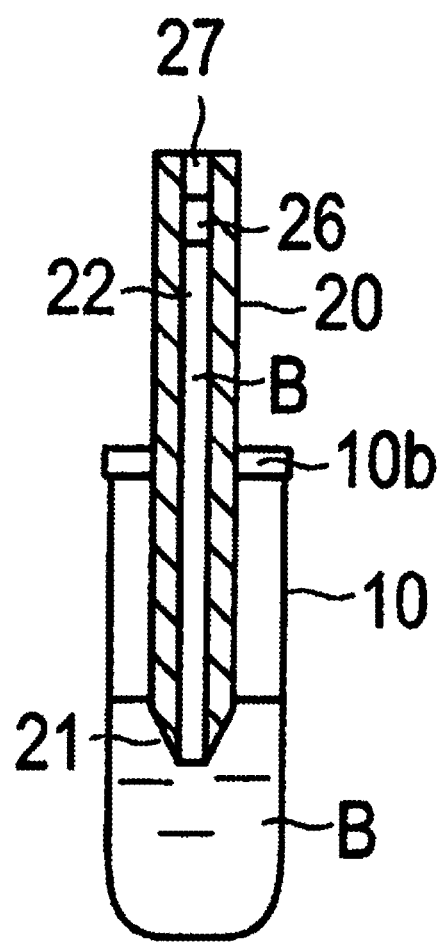
FIG. 7B illustrates a process of sucking blood.

Next, as illustrated in FIG. 7B, the puncture portion 21 of the suction tube 20 punctures the stopper 10b sealing the blood collecting tube 10, and then the blood B is sucked to the flow path in the suction tube 20. Consequently, the first waste area 23, the blood analysis area 24, and the second waste area 25 are filled with the blood (see FIG. 2). For example, 40 microliter of blood B is sucked into the suction tube 20.

Figure 7C:
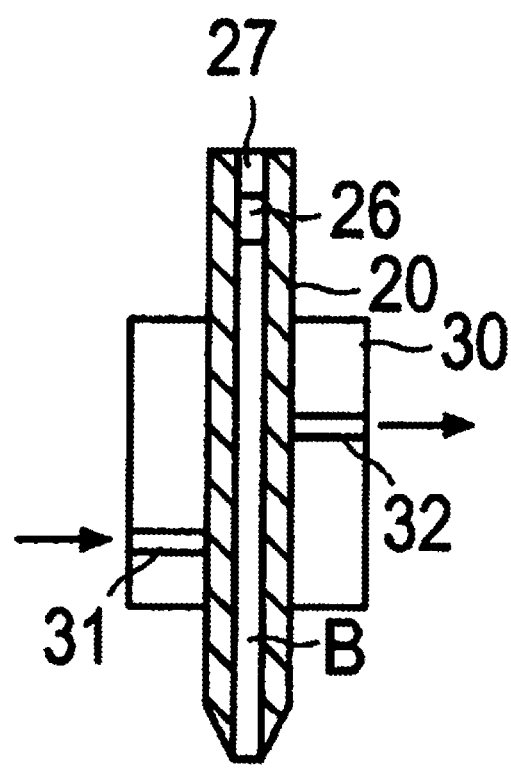
FIG. 7C illustrates a process of sucking blood.
Figure 7C:
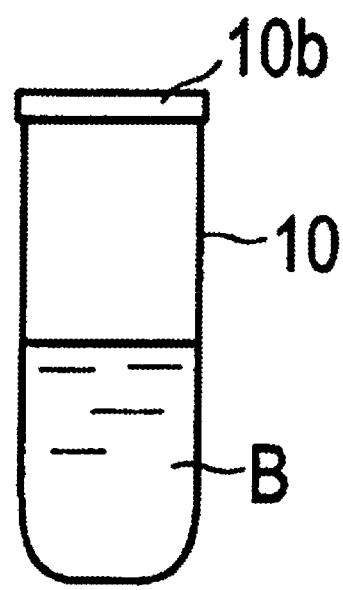

Subsequently, as illustrated in FIG. 7C, the suction tube 20 is removed from the blood collecting tube 10. At this time, the dilute solution is fed from the storage unit 70 to the passing portion 31 of the washing unit 30 and is discharged out from the passing portion 32. Thus, the dilute solution is fed to the outer circumference of the suction tube 20, so that the outer circumference of the suction tube 20 is washed and the blood attached to the suction tube at the time of being sucked is removed.

Figure 7D:
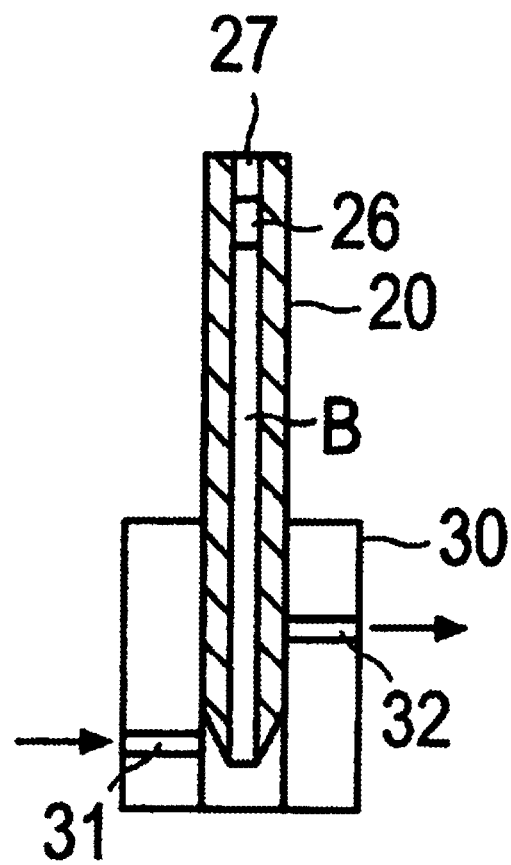
FIG. 7D illustrates a process of sucking blood.
Figure 7D:
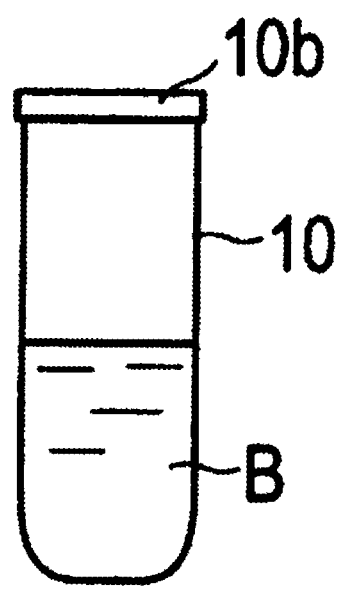

Next, as illustrated in FIG. 7D, the dilute solution is fed to the passing portion 31 and then is discharged out from the passing portion 32. Simultaneously, among the blood in the suction tube 20, the blood placed in the first waste area 23 is discarded (see FIG. 2). At this time, for example, 2 microliter of blood is discarded.

Figure 7E:
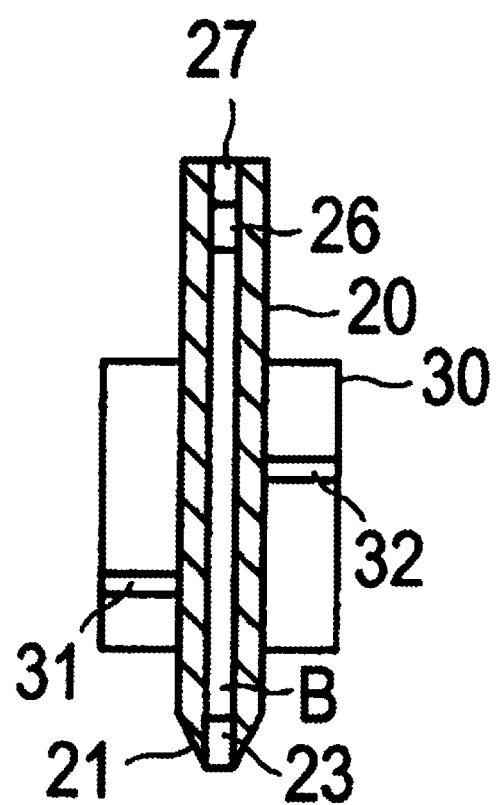
FIG. 7E illustrates a process of sucking blood.

Thereafter, as illustrated in FIG. 7E, the puncture portion 21 of the suction tube 20 protrudes downward from the washing unit 30. The process of step S02 has been described above.

Next, the sample is prepared to analyze the blood (S03). At step S03, the sample for the 3-classification of leukocytes, the sample for counting the erythrocytes and the blood platelets, and the sample for the 5-classification of leukocytes are prepared.

Subsequently, the amount of hemoglobin (HGB), the turbidity, or the absorbance of the sample in the second chamber 42 are measured by the second measuring unit 62 (S04). The light receiving element 623 transmits data on the intensity of the received light to the control unit 80. Further, the control unit 80 calculates the amount of hemoglobin (HGB), the turbidity, or the absorbance of the sample in the second chamber 42 based on the data on the intensity of the light received by the light receiving element 623.

Next, the sample in the fourth chamber 41 is delivered to the first chamber 40 (S05).

Subsequently, the amount of hemoglobin (HGB), the turbidity, or the absorbance of the sample in the first chamber 40 are measured by the first measuring unit 61 (S06). The light receiving element 613 transmits data on the intensity of the received light to the control unit 80. Further, the control unit 80 calculates the amount of hemoglobin (HGB), the turbidity, or the absorbance of the sample in the first chamber 40 based on the data on the intensity of the light received by the light receiving element 613.

Next, the sample prepared at step S03 is delivered to each of the three analysis units 51, 52, and 53 (S07). The three analysis units 51, 52, and 53 analyze the blood, respectively (S08). This will be described below in detail. Further, before the sample is delivered to the three analysis units 51, 52, and 53, the chamber 515 and a flow cell 521 are preferably washed as pre-treatment.

The sample stored in the fourth chamber 41 is delivered to the first analysis unit 51. The first analysis unit 51 performs the 3-classification of leukocytes using the above-described electric resistance method. That is, in this process, the 3-classification of leukocytes is performed using the blood stored in the first area 241 of the blood analysis area 24. Data on the 3-classification of leukocytes is transmitted to the control unit 80.

The sample stored in the third chamber 43 is delivered to the third analysis unit 53. The third analysis unit 53 counts the blood cells using the above-described electric resistance method. That is, in this process, the blood cells are counted using the blood stored in the third area 243 of the blood analysis area 24. Data on the counting of the blood cells is transmitted to the control unit 80.

The sample stored in the second chamber 42 is delivered to the second analysis unit 52. The second analysis unit 52 performs the 5-classification of leukocytes by the above-described flow cytometry. That is, in this process, the 5-classification of leukocytes is performed using the blood stored in the second area 242 of the blood analysis area 24.

Further, data on the 5-classification of leukocytes is delivered to the control unit 80. The process of steps S07 and S08 has been described above.

Next, the short sample of blood is detected by the control unit 80 (S09). In this process, the short sample of blood is detected based on the amount of hemoglobin (HGB), the turbidity, or the absorbance in the second chamber 42 measured at S04, and the amount of hemoglobin (HGB), the turbidity, or the absorbance in the first chamber 40 measured at step S06.

To be more specific, the control unit 80 determines whether the amount of hemoglobin (HGB), the turbidity, or the absorbance measured in the first and second chambers 40 and 42 are predetermined values or more. Further, the control unit 80 calculates a ratio of the amount of hemoglobin (HGB), the turbidity, or the absorbance measured in the first and second chambers 40 and 42, and determines whether an associated ratio is a predetermined threshold or less. Further, the control unit 80 calculates a differential in the amount of hemoglobin (HGB), the turbidity, or the absorbance measured in the first and second chambers 40 and 42, and may determine whether an associated differential is a predetermined threshold or less.

Here, when at least one of the amount of hemoglobin (HGB), the turbidity, and the absorbance measured in the first and second chambers 40 and 42 is less than a predetermined value, or the ratio of the amount of hemoglobin (HGB), the turbidity, or the absorbance measured in the first and second chambers 40 and 42 is a predetermined threshold or more, it is determined that the short sample of blood occurs.

Meanwhile, when each of the amount of hemoglobin (HGB), the turbidity, and the absorbance measured in the first and second chambers 40 and 42 is a predetermined value or more, and the ratio of the amount of hemoglobin (HGB), the turbidity, or the absorbance measured in the first and second chambers 40 and 42 is a predetermined threshold or less, it is determined that no short sample of blood occurs. That is, data on the 3-classification of leukocytes, data on the counted number of the erythrocytes, and data on the 5-classification of leukocytes, which are acquired by the three analysis units 51, 52, and 53, respectively, may be used as accurate blood information. The process of step S09 has been described above.

Finally, the dilute solution is delivered from the storage unit 70 to the pipe L, and the pipe L is washed (S10).

As described above, the blood analyzing method according to the embodiment uses the blood that is present in the first and second areas 241 and 242 of the blood analysis area 24, analyzes the blood, and detects the short sample of blood in the suction tube 20. Thus, even if the short sample of blood occurs in the blood analysis area 24, it is possible to detect the short sample of blood. Therefore, it is possible to detect the sample having the short sample of blood in the blood analysis area 24 and to prevent erroneous measurement results from being offered.

The first blood parameter is the amount of hemoglobin, the turbidity, or the absorbance, and the second blood parameter is the amount of hemoglobin, the turbidity, or the absorbance. Thus, it is possible to acquire the blood parameter in an easy manner, and it is easy to detect the short sample of blood.

The first area 241 is an area in one end of the blood analysis area 24, while the second area 242 is an area in the other end thereof. Thus, it is possible to detect the short sample of blood in the ends where the short sample of blood is likely to occur. Therefore, it is more preferable to detect the occurrence of the short sample of blood.

The invention is not limited to the above-described embodiment, and may be modified in various manners without departing from the scope of claims.

In the above-described embodiment, for example, the short sample of blood is detected using the blood that is present in the first and second areas 241 and 242. However, the short sample of blood may be detected using the blood that is present in the third area 243.

In the above-described embodiment, the number of erythrocytes is counted using the blood that is present in the third area 243. However, the invention also includes a case where the number of erythrocytes is not counted. That is, the blood analysis area 24 may include only the first area 241 and the second area 242. Alternatively, in addition to the first to third areas 241 to 243, an additional area of blood for analysis may be further formed in the blood analysis area 24.

In the above-described embodiment, the amount of hemoglobin (HGB), the turbidity, or the absorbance of the sample in the second chamber 42 is measured, the amount of hemoglobin (HGB), the turbidity, or the absorbance of the sample in the first chamber 40 is measured, and the blood is thus analyzed. However, this order is not limited particularly.

The present application is based on Japanese Patent Application No. 2015-131849, filed on Jun. 30, 2015, the entire contents of which are incorporated herein by reference.

INDUSTRIAL APPLICABILITY

There is provided with a method and an apparatus for analyzing blood, capable of preventing erroneous measurement results from being offered.

REFERENCE SIGNS LIST

1 blood analyzing apparatus
10 blood collecting tube
20 suction tube
30 washing unit
40 first chamber
41 fourth chamber
43 second chamber
43 third chamber
51 first analysis unit
52 second analysis unit
53 third analysis unit
61 first measuring unit
62 second measuring unit
80 control unit (detecting unit)

What is claimed is:

1. A blood analyzing apparatus comprising:
a suction tube that is used to suck blood;
a first chamber to which the blood is discharged from the suction tube;
a first measuring unit that measures a first blood parameter using the blood discharged to the first chamber;
a second chamber to which the blood is discharged from the suction tube;
a second measuring unit that measures a second blood parameter in the second chamber using the blood discharged to the second chamber;
a detecting unit that detects a short sample of blood in the suction tube when blood is sucked by the suction tube;
a first analysis unit that measures first leukocytes;
a second analysis unit that measures second leukocytes;
a third chamber to which the blood is discharged from the suction tube;
a third analysis unit that counts erythrocytes using the blood discharged to the third chamber; and
a fourth chamber to which the blood is discharged from the suction tube,
wherein the first analysis unit measures the first leukocytes by using the blood delivered from the fourth chamber,
wherein the second analysis unit measures the second leukocytes by using the blood delivered from the second chamber, and
wherein the detecting unit detects the short sample of blood based on the first blood parameter and the second blood parameter.

2. The blood analyzing apparatus according to claim 1, wherein the first blood parameter includes amount of hemoglobin, turbidity, or absorbance, and the second blood parameter includes amount of hemoglobin, turbidity, or absorbance.

3. The blood analyzing apparatus according to claim 1, wherein
the blood located in the suction tube at one end of a blood analysis area and sucked by the suction tube is discharged to the first chamber; and
the blood located at the other end of the blood analysis area and sucked by the suction tube is discharged to the second chamber.

4. The blood analyzing apparatus according to claim 2, wherein
the blood located in the suction tube at one end of a blood analysis area and sucked by the suction tube is discharged to the first chamber; and
the blood located at the other end of the blood analysis area and sucked by the suction tube is discharged to the second chamber.

5. The blood analyzing apparatus according to claim 1, wherein the second measuring unit measures the second blood parameter selected from the group consisting of an amount of hemoglobin (HGB), turbidity, absorbance, or a combination thereof.

6. A blood analyzing apparatus comprising:
a suction tube that is used to suck blood;
a first chamber;
a first measuring unit that measures a first blood parameter using the blood discharged to the first chamber from a fourth chamber;
a second chamber to which the blood is discharged from the suction tube;
a second measuring unit that measures a second blood parameter using the blood discharged to the second chamber;
a detecting unit that detects a short sample of blood in the suction tube when blood is sucked by the suction tube;
a first analysis unit that measures first leukocytes;
a second analysis unit that measures second leukocytes;
a third chamber to which the blood is discharged from the suction tube;
a third analysis unit that counts erythrocytes using the blood discharged to the third chamber; and
the fourth chamber to which the blood is discharged from the suction tube,
wherein the first analysis unit measures the first leukocytes by using the blood delivered from the fourth chamber, wherein the second analysis unit measures the second leukocytes by using the blood delivered from the second chamber, and wherein the detecting unit detects the short sample of blood based on the first blood parameter and the second blood parameter.

\* \* \* \* \*